(12) United States Patent
Awad et al.

(10) Patent No.: US 9,637,807 B1
(45) Date of Patent: May 2, 2017

(54) SYNTHESIS OF METAL NANOPARTICLES USING AN EXTRACT OF TERFEZIACEAE

(71) Applicant: KING SAUD UNIVERSITY, Riyadh (SA)

(72) Inventors: Manal Ahmed Gasmelseed Awad, Riyadh (SA); Ebtesam Mohammed Al Olayan, Riyadh (SA); Sarah Saleh Abdulla Alsaif, Riyadh (SA); Muzzammil Iqbal Siddiqui, Riyadh (SA); Manal Fawzy Elkhadragy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/147,873

(22) Filed: May 5, 2016

(51) Int. Cl.
| A61K 36/06 | (2006.01) |
| A61K 36/062 | (2006.01) |
| C22B 3/00 | (2006.01) |
| A61K 9/16 | (2006.01) |
| A61K 33/38 | (2006.01) |
| A01N 59/16 | (2006.01) |
| A01N 25/12 | (2006.01) |

(52) U.S. Cl.
CPC .............. *C22B 11/04* (2013.01); *A01N 25/12* (2013.01); *A01N 59/16* (2013.01); *A61K 9/1688* (2013.01); *A61K 33/38* (2013.01)

(58) Field of Classification Search
CPC .................................................. A61K 36/062
USPC ...................................................... 424/195.15
See application file for complete search history.

(56) References Cited

U.S. PATENT DOCUMENTS

| 8,057,682 | B2 | 11/2011 | Hoag et al. | |
| 2006/0269485 | A1* | 11/2006 | Friedman | A61K 9/107 424/45 |
| 2007/0292355 | A1* | 12/2007 | Tamarkin | A61K 9/12 424/43 |
| 2007/0292461 | A1* | 12/2007 | Tamarkin | A61K 8/86 424/401 |
| 2008/0299220 | A1* | 12/2008 | Tamarkin | A61K 9/0014 424/600 |

OTHER PUBLICATIONS

Enshasy et al. Evidence-Based Complementary and Alternative Med. 2013. Review Article. Article ID 620451, 10 pages.*

* cited by examiner

*Primary Examiner* — Chris R Tate
(74) *Attorney, Agent, or Firm* — Richard C. Litman

(57) ABSTRACT

A method of preparing metal nanoparticles using an extract of desert truffles (Terfeziaceae) includes providing an aqueous solution including a metal salt; and combining an extract of Terfeziaceae with the aqueous metal salt solution to produce the metal nanoparticles. The metal salt can be silver nitrate ($AgNO_3$) and the metal nanoparticles can be silver nanoparticles. The metal nanoparticles can have a mean diameter in the range of from about 5 nm to about 100 nm. The silver nanoparticles can be used as an antimicrobial agent and/or an anti-parasitic agent.

7 Claims, 11 Drawing Sheets

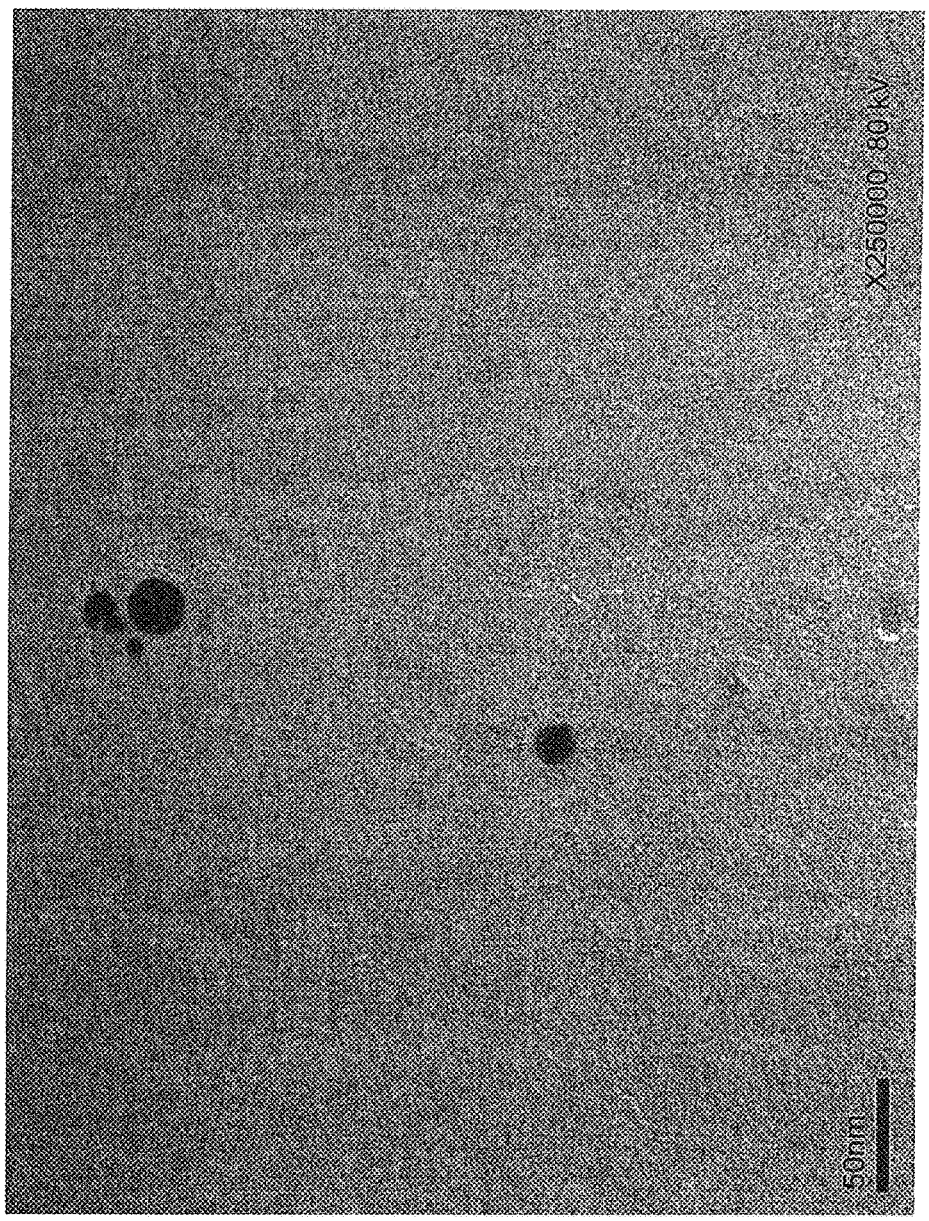

SYNTHESIS OF METAL NANOPARTICLES USING AN EXTRACT OF TERFEZIACEAE

BACKGROUND OF THE INVENTION

1. Field of the Invention

The present invention relates to green synthesis of metal nanoparticles, and particularly, to synthesis of silver nanoparticles using desert truffles (Terfeziaceae) as a reducing agent.

2. Description of the Related Art

Nanotechnology is emerging as a rapidly growing field with its application in science and technology for the purpose of manufacturing new materials at the nanoscale level. Nanoparticles exhibit completely new or improved properties compared to their corresponding bulk materials. Because of their size, catalytic property, ability to deliver drug, increased efficacy, and decreased toxicity, nanotechnology finds applications in various fields including healthcare, defense and day-to-day life. Because the nanoparticles possess a very high surface to volume ratio, they are particularly useful in applications where high surface areas are critical for success.

Nanomaterials can be synthesized by various methods such as heat evaporation, non-sputtering, solvothermal reduction, electrochemical technique, chemical reduction, photochemical, reverse micelles, thermal decomposition, radiation assisted, electrochemical, and sonochemical including microwave assisted method. However, surface passivator reagents such as thiophenol, thiourea, macro captoacetate, which are used to prevent nanoparticles from aggregation, pollute the environment.

Nanomaterials can also be synthesized from environmentally friendly "green" biological methods. When compared to nanoparticles manufactured from chemicals, for example, nanoparticles made from "green" methods are more eco-friendly, readily available, cost effective and have little if any side effects. Biosynthesis of nanoparticles using leaves extracts of *Murraya koenigii*, *Eucalyptus hybrida*, *Artocarpus heterophyllus*, *Camellia Sinensis*, *Mollugo nudicaulis* and *Panicum virgatum* have been disclosed. Additionally, biosynthesis of nanoparticles using fruit extracts of *Capsicum annum* L., *Carica papaya*. L., *Citrullus colocynthis* and *Lantana camara* have been disclosed. Due to their high antimicrobial activity, silver nanoparticles can be used in a variety of applications, including food, medicine, clothing, sunscreens and cosmetics.

Thus, a method of producing metal nanoparticles utilizing desert truffles (Terfeziaceae) aqueous extract thereby solving the aforementioned problems is desired.

SUMMARY OF THE INVENTION

A method of preparing metal nanoparticles using an extract of desert truffles (Terfeziaceae) includes providing an aqueous solution including a metal salt and combining an extract of the Terfeziaceae with the aqueous metal salt solution to produce the metal nanoparticles. The metal salt can be silver nitrate ($AgNO_3$) and the metal nanoparticles can be silver nanoparticles having a mean diameter in the range of from about 5 nm to about 100 nm.

These and other features of the present invention will become readily apparent upon further review of the following specification and drawings.

BRIEF DESCRIPTION OF THE DRAWINGS

FIGS. 1A and 1B show transmission electron microscopy (TEM) images of green silver nanoparticles synthesized according to the present teachings.

Similar reference characters denote, corresponding features consistently throughout the attached drawings.

DETAILED DESCRIPTION OF THE PREFERRED EMBODIMENTS

Figure 1B:
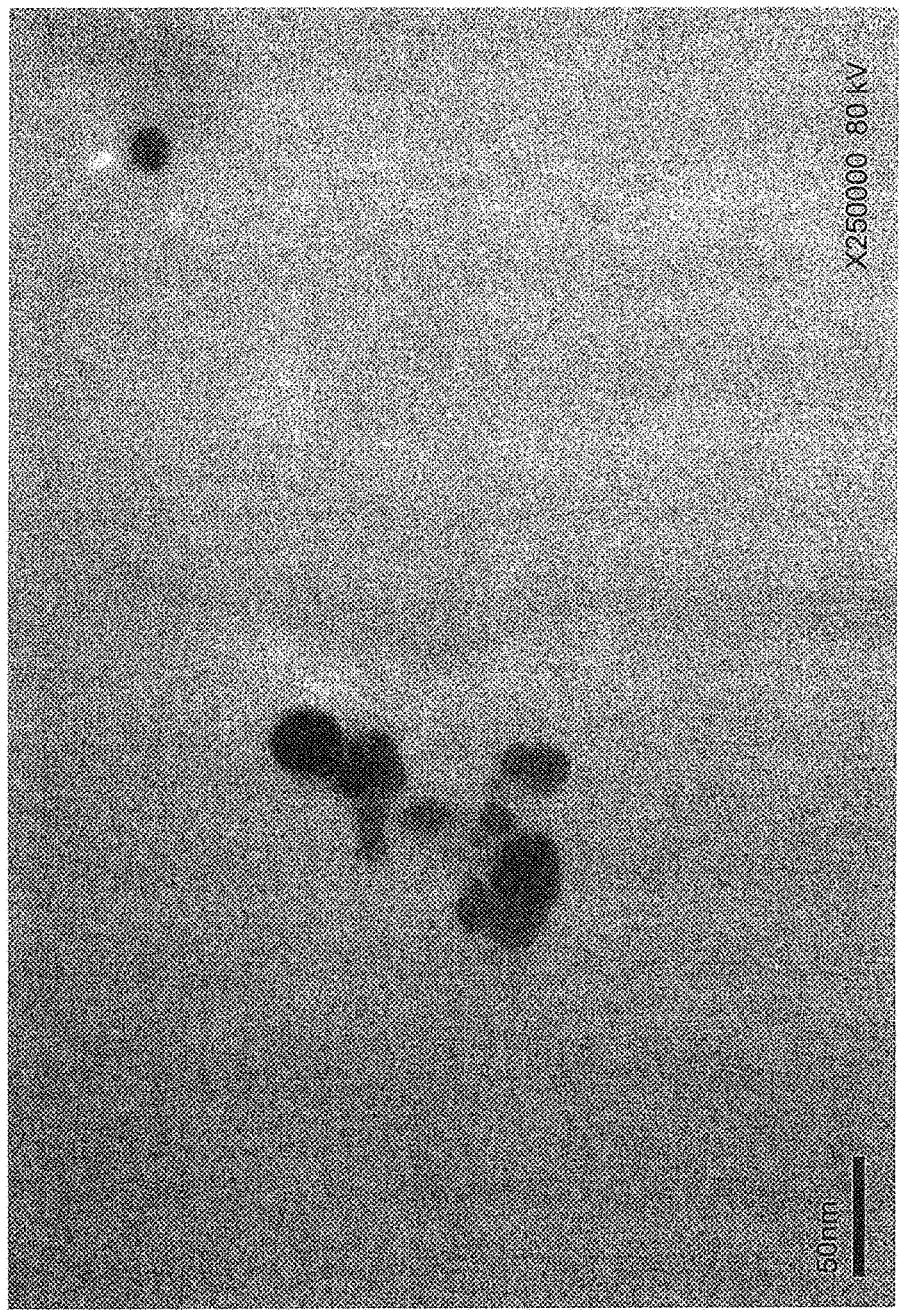

A method for preparing metal nanoparticles includes combining an aqueous solution including a metal salt with an extract of desert truffles (Terfeziaceae) to produce the metal nanoparticles. The metal salt can be, for example, silver nitrate ($AgNO_3$) and the resulting metal nanoparticles can be silver nanoparticles. The aqueous solution of metal salt can be prepared by dissolving about 1 mmole/ml silver nitrate ($AgNO_3$) solution in about 50 ml of water. The extract of desert truffles (Terfeziaceae) can be an aqueous extract. The silver nanoparticles can have a mean diameter in the range of from about 5 nm to about 100 nm. The silver nanoparticles can be spherical, spheroidal, elongated spherical, rod-shaped, and/or faceted-shape. The silver nanoparticles can be used as an antimicrobial or as an anti-parasitic agent.

The aqueous extract of desert truffles (Terfeziaceae) can be prepared by washing fruit bodies of Terfeziaceae, chopping the fruit body of Terfeziaceae to provide finely chopped pieces of the Terfeziaceae; adding water to the chopped pieces of the Terfeziaceae in a vessel and boiling for about 1-5 minutes to provide an aqueous Terfeziaceae mixture; pulverizing the aqueous Terfeziaceae mixture using a grinder to obtain a crushed Terfeziaceae mixture; centrifuging the crushed Terfeziaceae mixture for about 5 to 10 minutes at about 8000 rpm at room temperature; and filtering the Terfeziaceae mixture to obtain an aqueous extract of Terfeziaceae.

As used herein, the term "nanoparticle" refers to a particle having at least one dimension and sized between 1 and 100 nanometers. The metal nanoparticles described herein can be silver nanoparticles. The silver nanoparticles can be from about 5 nm to about 100 nm in diameter, and preferably from about 20 non to about 30 nm in diameter. The silver nanoparticles can be effective as an antimicrobial or as an anti-parasitic agent. The method of producing silver nanoparticles using the extract of desert truffles (Terfeziaceae) is a green, simple, cost effective and affordable method, which can easily be scaled up for large scale synthesis.

The following examples will further illustrate the process of making the metal (silver) nanoparticles from desert truffles (Terfeziaceae).

Example 1

Preparing an Aqueous Extract of Desert Truffles (Terfeziaceae)

Fresh desert truffles (Terfeziaceae) were obtained from local commercial sources in Saud Arabia. About 5 g of Terfeziaceae were washed carefully and thoroughly with double distilled water to remove any dirt particles, and then cut into small pieces. About 50 ml of boiling distilled water was added to the cut pieces in a vessel and then boiled for 1-2 minutes. The mixture was crushed by a mixer, centrifuged for about 7 minutes at about 8000 rpm at room temperature, and then filtered. The resultant filtrate extract of Terfeziaceae was kept in a refrigerator (4° C.) until used. The resultant filtrate extract of Terfeziaceae was used for the reduction of $Ag^+$ to $Ag^0$.

Example 2

Synthesis of Silver Nanoparticles

Figure 2:
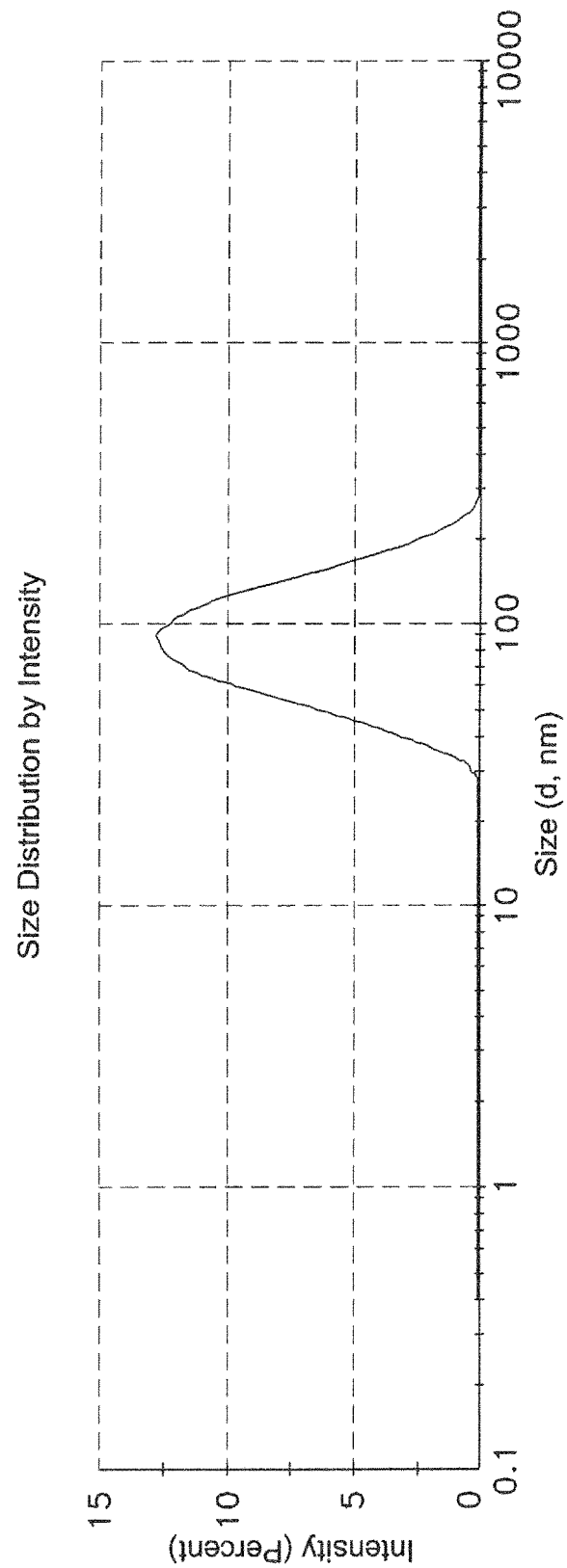
FIG. 2 is a graph showing the particle average size determination by Zetasizer for the silver nanoparticles synthesized according to the method of the present invention.

About 1 mmol/ml silver nitrate ($AgNO_3$) was dissolved in 50 ml of distilled water and stirred vigorously at 90° C. for 5 minutes to provide a silver nitrate solution. Thereafter, about 5 ml of the desert truffles extract (from Example 1) was added to the silver nitrate solution resulting in a color change from colorless to dark brown. The change of color of the solution from colorless to dark brown indicated the reduction of silver ions and the formation of silver nanoparticles. FIGS. 1A and 1B show the transmission electron microscopy (TEM) images of the silver nanoparticles produced by the present method. FIG. 2 shows the particle average size determination by Zetasizer for the silver nanoparticles synthesized according to the present method. A single peak with a diameter of 95.75 nm was found.

Example 3

Antimicrobial Activity Study

The following bacterial strains were used for the trials. *Bacillus cereus, Bacillus subtilis, Enterococcus aerogenes, Serratia marcecens, Staphylococcus aureus, Aeromonas hydrophila, Micrococcus luteus, Proteus vulgaris, Salmonella typhimurium, Escherichia coli, Lelerichia* sp., and *Listeria monocytogenes*. The bacterial strains were all obtained from Department of Food Science and Nutrition, College of Food and Agricultural Sciences, King Saud University. The antibacterial activity for the silver nanoparticles was determined by using agar well diffusion method. Bacterial concentrations were prepared for each bacteria in normal Ringlers solution at a concentration of 108/ml. Then, wells were made in Muller Hinton agar by using a cork borer sized 8 mm in diameter. Plates were cultured by using small swabs of each bacteria. 100 μl of the silver nanoparticles, 100 μl of the desert truffles (Terfeziaceae) extract and 100 μl of methanol as control were each introduced into the wells. The inoculated plates were incubated at 37° C. for 24 hrs. The diameters of inhibition zones were measured for each plate. The pure methanol was used as control for all the tested strains.

Example 4

Parasite Viability Assay (MTT)

*Leishmania major* were cultured in 96 wells plate at a density of $2\times10^5$ parasite/well in 100 μl optimized medium. The parasite was allowed to culture for 24 hours before being treated with individual concentrations of green nanoparticles i.e. (15 mM, 20 mM and 25 mM). Treated parasites were allowed to grow further for 24 hours, 48 hours and 72 hours. At the end of the incubation period and concentration point, 100 μl of 0.22 μm filter-sterilized of 3-(4, 5-dimethylthiazol-2-yl)-2,5-diphenyltetrazolium bromide (MTT, Sigma Aldrich, UK) was added at 26° C. at a final concentration 5 mg/ml. The 96 wells plate was kept in the dark for 3 hours before the medium containing MTT was removed. 100 μl Dimethyl sulfoxide (DMSO; Ajax Finechem Pty Ltd, Australia) was added to dissolve formazan crystals. The 96-well-plate was also shaken for 15 minutes in the dark to help dissolve the formazan crystals. The optical density (O.D.) of each treatment was measured at 570 nm using Lab systems Multiskan EX Version 3.0 (Helsinki, Finland). Each experiment was performed in three replicates.

Values of optical densities were normalized according to the control (untreated parasites). Therefore, parasite viability values of untreated parasites should be 100% while values of treated parasites have values below or above 100%. The following equation was used for calculations:

Parasite Viability (%)=(Absorbance of individual treatment/Absorbance of the control)×100

Table 1 shows the parasite viability % in different concentrations of nanoparticles and control at the exposure time of 24, 48 and 72 hours.

TABLE 1

| Concentrations (mM) | 24 Hours | 48 Hours | 72 Hours |
|---|---|---|---|
| 15 | 61.11111111 | 63.04347826 | 39.0625 |
| 20 | 68.51851852 | 65.2173913 | 45.3125 |
| 25 | 51.85185185 | 39.13043478 | 40.625 |
| Control | 100 | 100 | 100 |

Figure 3:
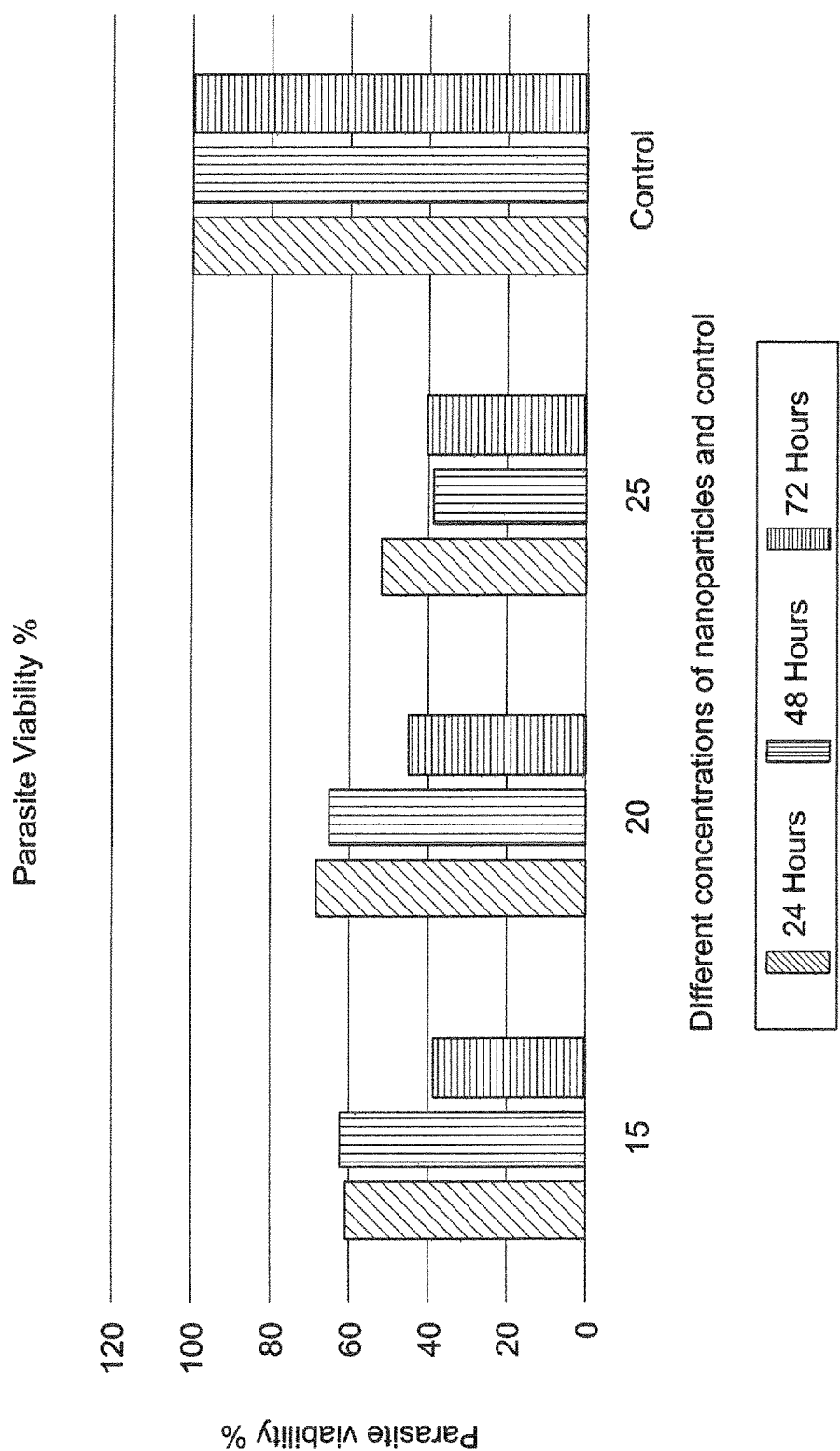
FIG. 3 is a graph showing the parasite viability percentage (%) on exposure to three different concentrations of nanoparticles at 24, 48 and 72 hours.
Figure 4A:
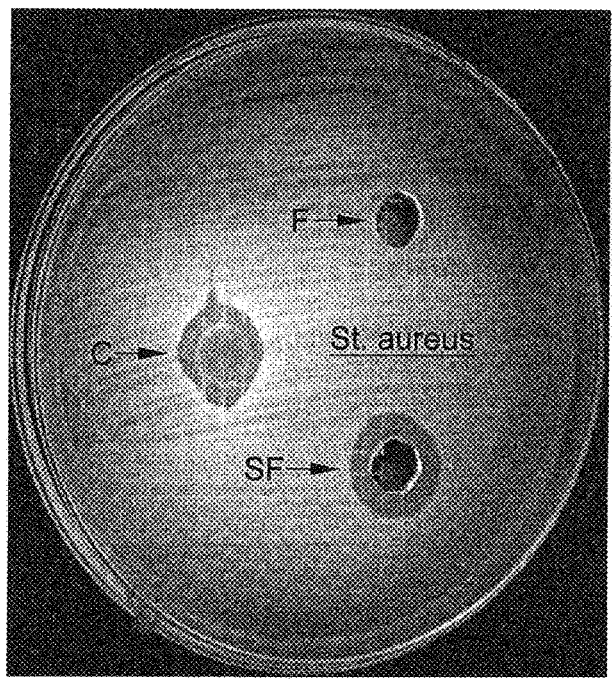
FIGS. 4A-4M show the zones of inhibition of the silver nanoparticles against different bacterial strains.
Figure 4B:
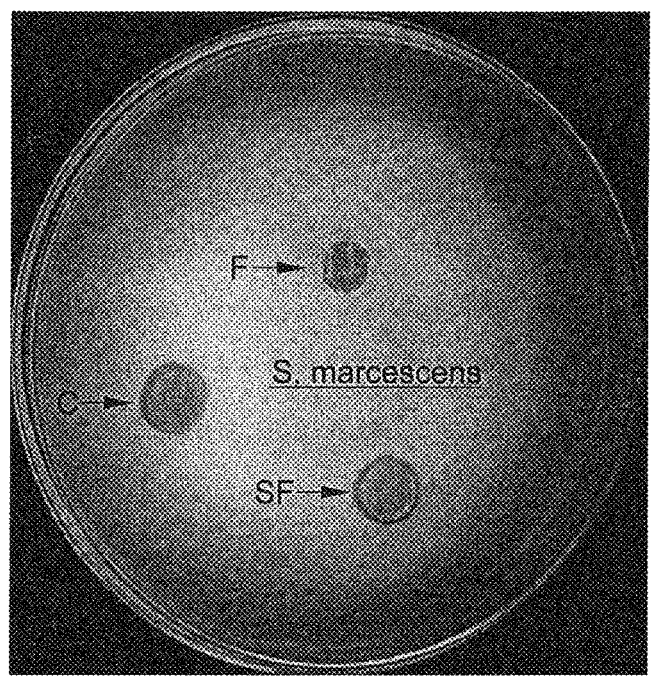
Figure 4C:
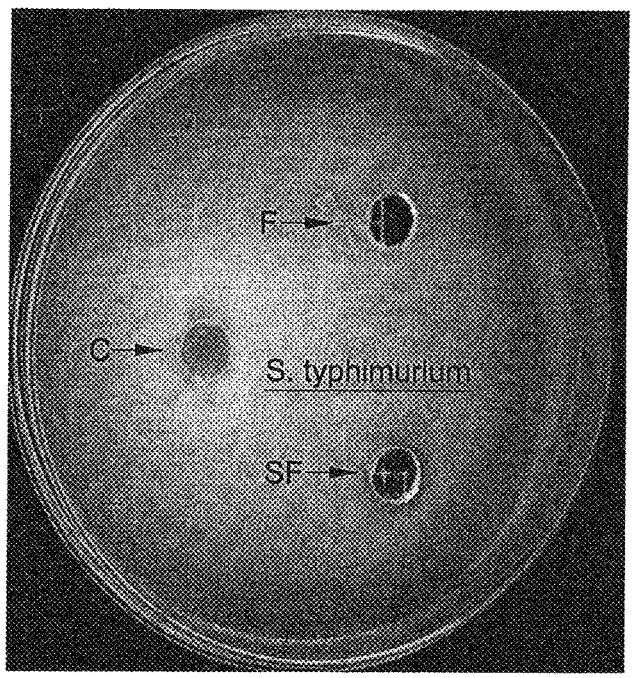
Figure 4D:
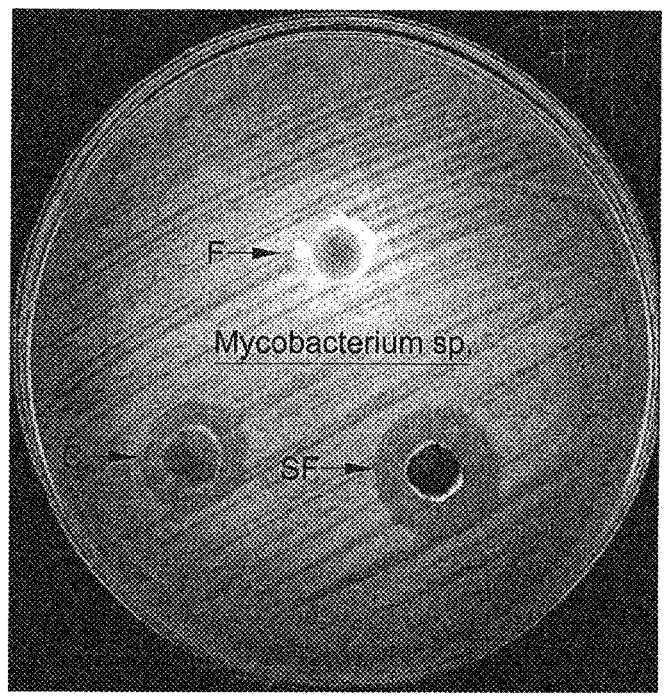
Figure 4E:
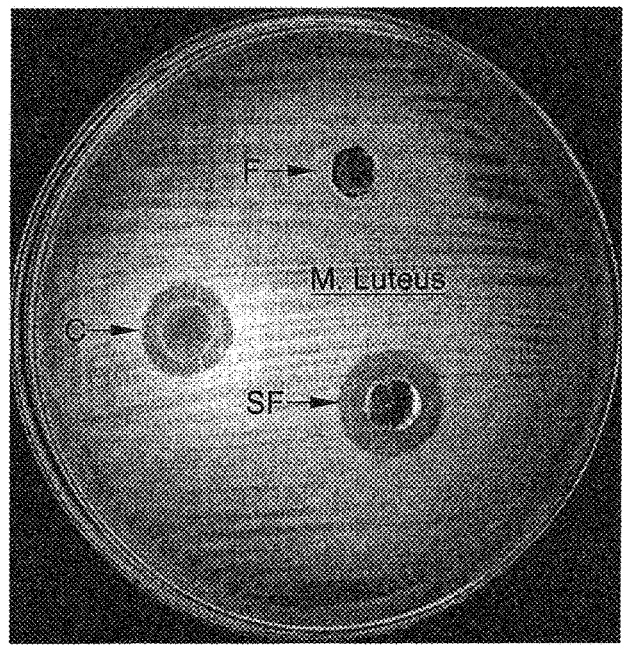
Figure 4F:
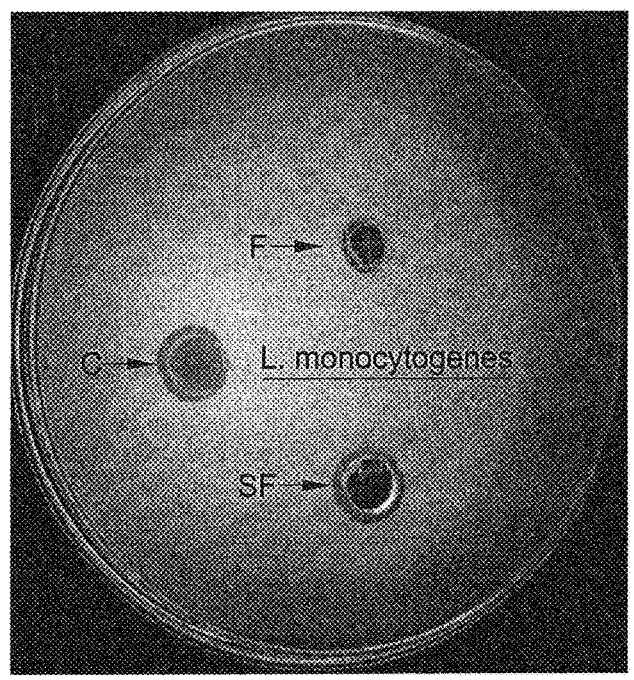
Figure 4G:
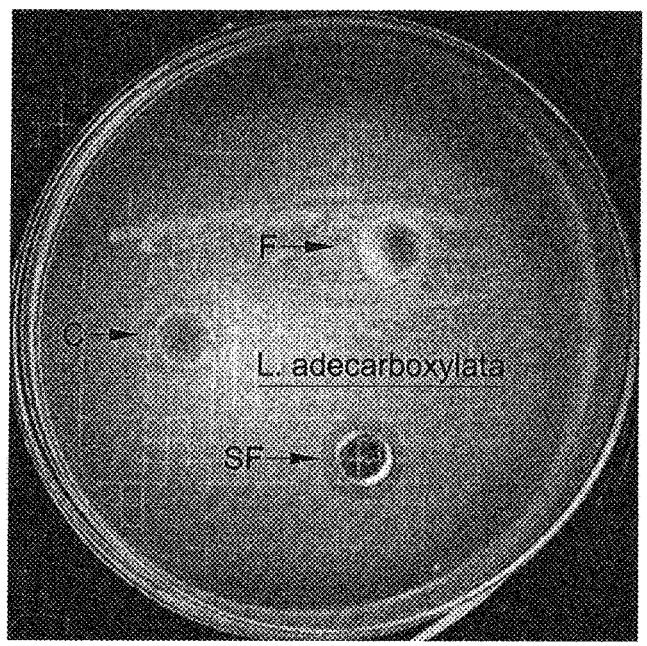
Figure 4H:
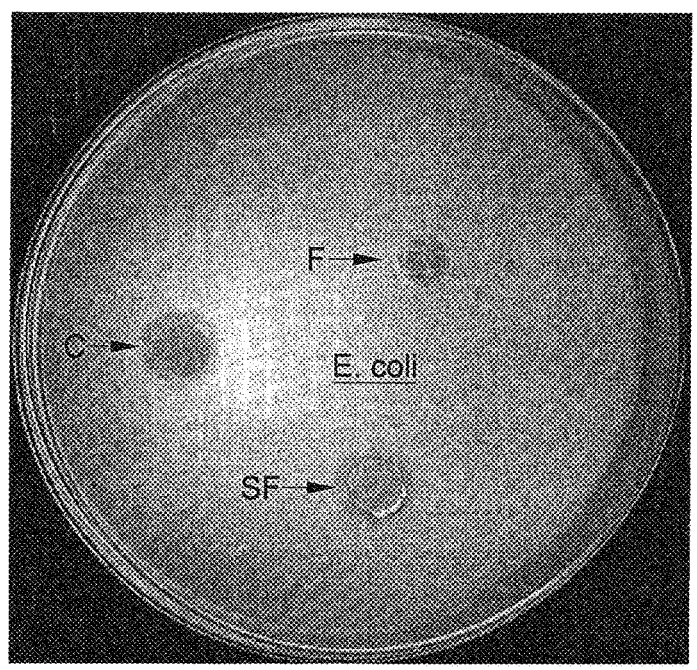
Figure 4I:
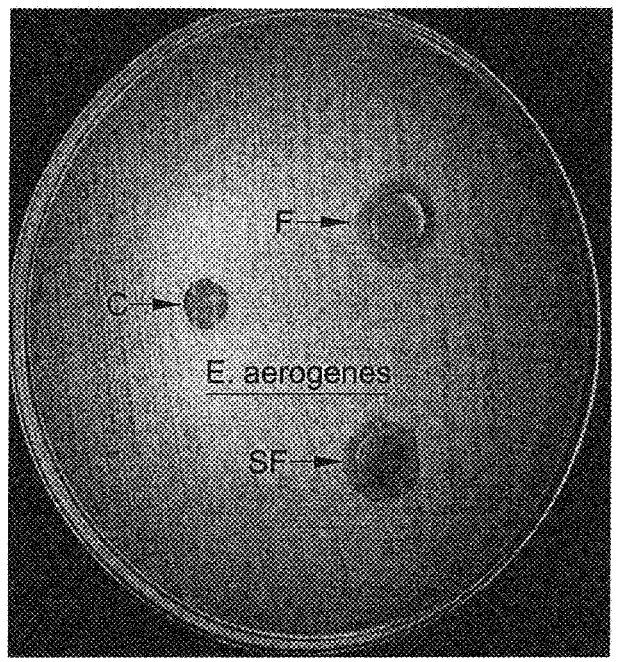
Figure 4J:
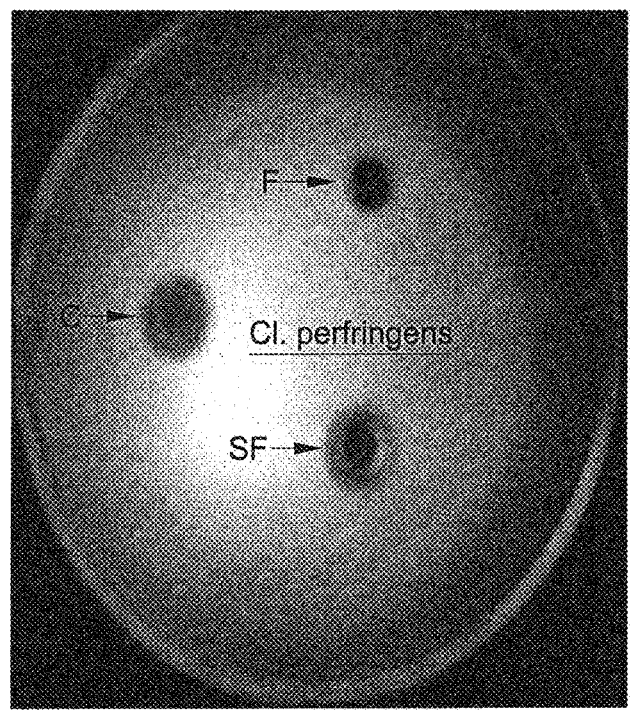
Figure 4K:
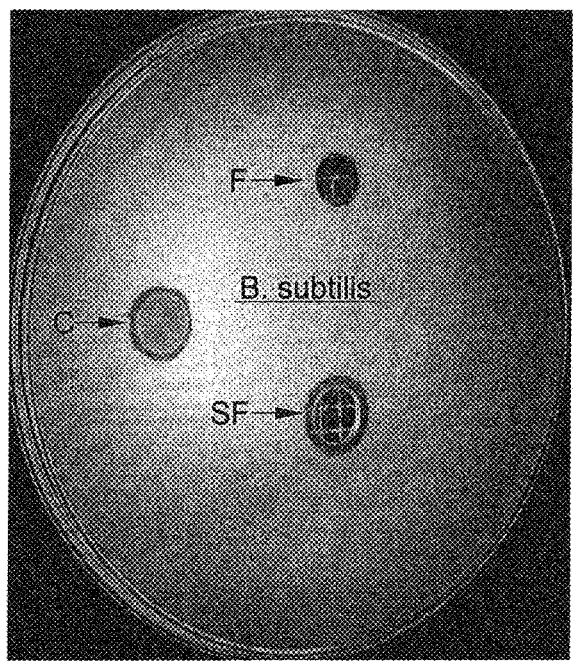
Figure 4L:
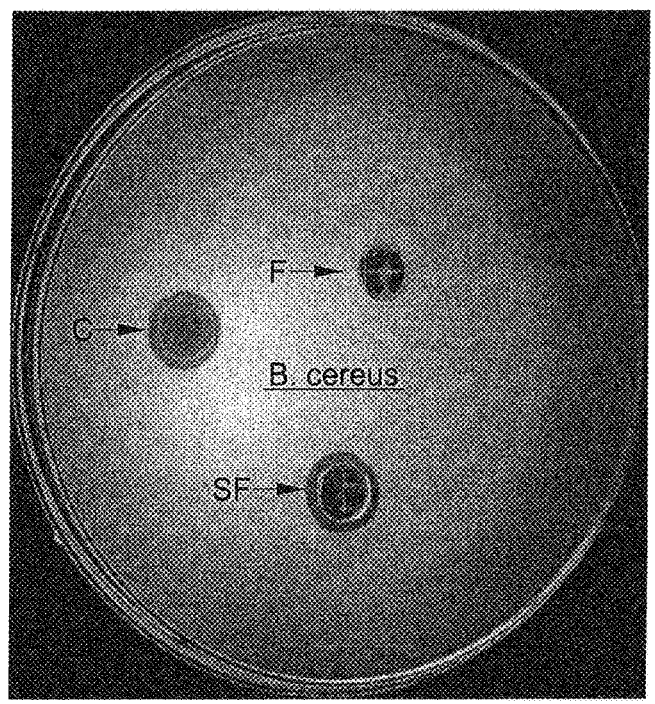
Figure 4M:
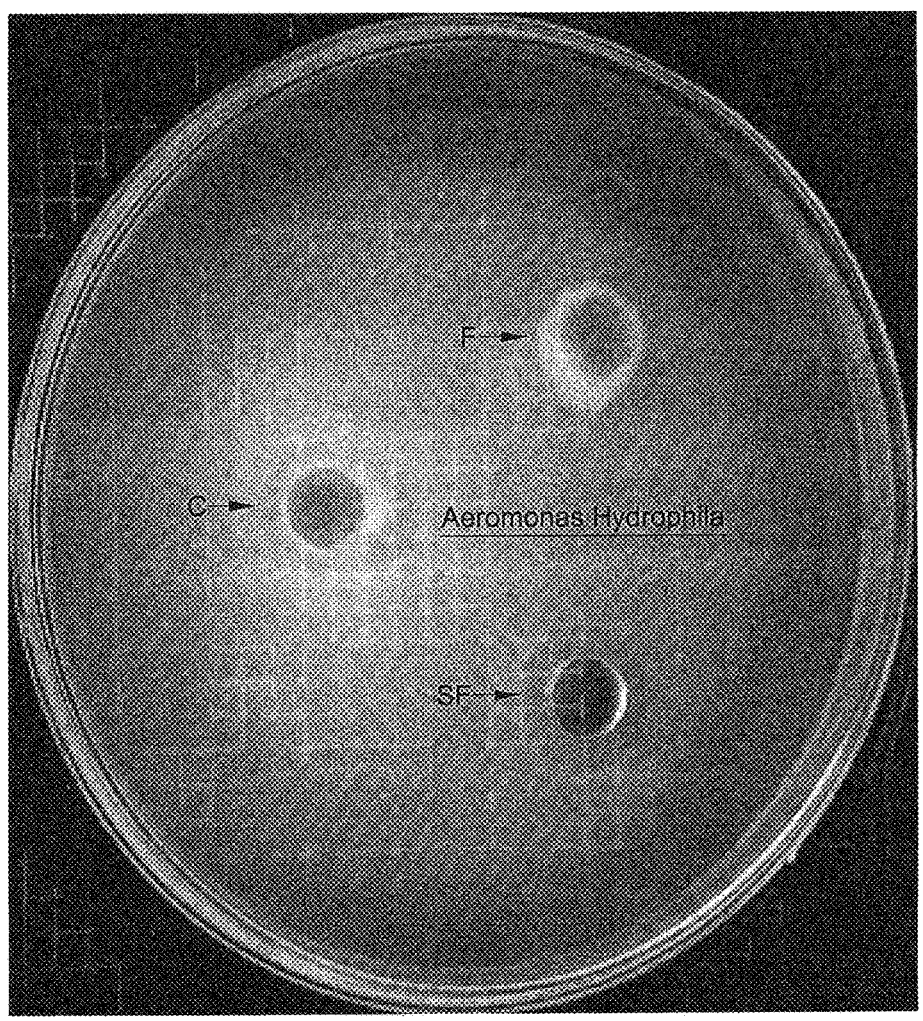

FIG. 3 shows the parasite viability percentage (%) on exposure to three different concentrations of nanoparticles at 24, 48 and 72 hours. FIGS. 4A-4M show the zones of inhibition of green silver nanoparticles against the different bacterial strains indicated in the figure. The area marked with the letter "F" represents the zones of inhibition of desert truffles (Terfeziaceae) extract. The area marked with the letters "SF" represents the zones of inhibition for silver nanoparticles synthesized by desert truffles (Terfeziaceae) extract. The area marked with the letter "C" represents methanol as control.

It is to be understood that the present invention is not limited to the embodiments described above, but encompasses any and all embodiments within the scope of the following claims.

We claim:

1. A method for the synthesis of metal nanoparticles containing an extract of Terfeziaceae comprising the steps of:
   a) adding about 5 g of Terfeziaceae (desert truffles) fruiting bodies to about 50 ml of water to form an aqueous Terfeziaceae mixture, and boiling the aqueous Terfeziaceae mixture for about 1-5 minutes to obtain a Terfeziaceae extract;
   b) dissolving about 1-5 mmol/ml silver nitrate ($AgNO_3$) in about 50 ml of water to obtain a silver nitrate solution; and
   c) forming said silver nanoparticles by adding about 5 ml of the Terfeziaceae extract to the silver nitrate solution, resulting in a color change of the solution from colorless to dark brown due to a reduction of silver ions in the solution.

2. The method according to claim 1, wherein the Terfeziaceae extract and the silver nitrate solution are mixed at a temperature ranging from about 60° C. to about 100° C.

3. The method according to claim 1, wherein the silver nanoparticles are from about 5 nm to about 100 nm in diameter.

4. The method according to claim 1, wherein the silver nanoparticles have a mean diameter in the range of from about 20 nm to about 30 nm.

5. The method according to claim 1, wherein the silver nanoparticles are spherical, spheroidal, elongated spherical, rod-shaped, and/or faceted.

6. A method for inhibiting growth of a microorganism comprising contacting the microorganism with an effective amount of the silver nanoparticles produced according to the method of claim 1.

7. A method for inhibiting growth of a microorganism comprising contacting the microorganism with an effective amount of the silver nanoparticles produced according to the method of claim 1.

* * * * *